United States Patent
Pratt et al.

(10) Patent No.: US 6,783,558 B2
(45) Date of Patent: Aug. 31, 2004

(54) HAIR COLORING METHOD AND COMPOSITION

(75) Inventors: Dominic Pratt, Darmstadt (DE); Toshio Kawagishi, Kanagawa (JP)

(73) Assignees: Kao Corporation, Tokyo (JP); Fuji Photo Film Co., Ltd., Kanagawa (JP)

( * ) Notice: Subject to any disclaimer, the term of this patent is extended or adjusted under 35 U.S.C. 154(b) by 173 days.

(21) Appl. No.: 10/096,669

(22) Filed: Mar. 14, 2002

(65) Prior Publication Data

US 2003/0024059 A1 Feb. 6, 2003

(30) Foreign Application Priority Data

| Mar. 15, 2001 | (DE) | .......................................... 101 12 436 |
| Mar. 24, 2001 | (DE) | .......................................... 101 14 545 |
| Jul. 31, 2001 | (JP) | ....................................... 2001-231327 |
| Aug. 1, 2001 | (EP) | .............................................. 01117774 |

(51) Int. Cl.$^7$ ................................................ A61K 7/13
(52) U.S. Cl. ...................... 8/405; 8/662; 8/677; 8/678; 8/690; 8/691; 8/692
(58) Field of Search ............................ 8/405, 662, 677, 8/678, 690, 691, 692, 406, 407, 421, 614

(56) References Cited

U.S. PATENT DOCUMENTS 6,197,071 B1   3/2001   Diehl et al. .................... 8/409

FOREIGN PATENT DOCUMENTS

| EP | 0 923 929 A1 | 11/1998 | | |
| EP | 1 275 367 A1 | 1/2001 | | |
| JP | 7-214922 | 8/1995 | | |
| JP | 7214922 | * 8/1995 | ............ | B41M/5/38 |
| JP | 7-304273 | 11/1995 | | |
| JP | 11-349874 | * 12/1999 | ............ | C09D/11/00 |

* cited by examiner

Primary Examiner—Yogendra N Gupta
Assistant Examiner—Eisa Elhilo
(74) Attorney, Agent, or Firm—Oblon, Spivak, McClelland, Maier & Neustadt, P.C.

(57) ABSTRACT

The present invention is directed to a hair coloring method by using a composition comprising a specified ring-fused heterocycle direct dyestuff having the general formula (1) or a salt thereof wherein the formulas are as defined in the patent claims.

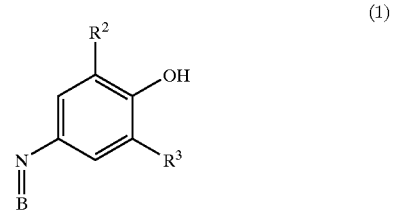

(1)

Furthermore, the present invention is also directed to the composition. This composition has a surprisingly good hair coloring performance and compatibility with peroxides. The use of this composition leads to long lasting brilliant colors wherein the color is stable against washing of the hair and environmental influences.

15 Claims, No Drawings

HAIR COLORING METHOD AND COMPOSITION

TECHNICAL FIELD

The present invention relates to a hair colouring method using a composition that comprises at least one specific direct dyestuff, which can impart a vivid and durable colour to the hair and is stable to oxidizing agents. In addition, the present invention also relates to the hair colouring composition.

BACKGROUND ART

Hair colouring compositions which comprise several anionic or cationic direct dyestuffs are well-known and, contrary to the permanent hair colouring compositions comprising oxidative dye intermediates, require no coupling reaction by oxidizing agents. This type of direct colouring composition is often applied to the hair in the form of a so-called tinting shampoo together with surface-active components, or is applied in the form of a lotion, emulsion or thickened solution such as a gel.

This direct hair colouring composition should, however, be improved in its colour durability and in particular colour intensity as well as uniformity of resulting colour and colour gloss. Additionally, the above-described direct dyestuffs generally have the drawback that they are not compatible with alkaline peroxides, so the direct hair colouring compositions are generally applied to the hair without peroxide. Accordingly, the direct hair colouring composition has no bleaching effect on the hair.

DISCLOSURE OF THE INVENTION

An object of the present invention is to provide a hair colouring method using a composition, on the basis of direct dyestuffs, which shows excellent dyeing characteristics and gives to the hair a durable and vivid colour over time and which can be applied to the hair in the form of a lotion, emulsion, solution, gel, suspension or also an aerosol by adding propellants.

Another object of the present invention is to provide a hair colouring method using a composition that also supplies hair bleaching power coupled with the above-described performance, based on the direct dyestuffs.

The solution to these objects is a hair colouring method using a composition comprising at least one specific direct dyestuff that has good hair colouring performance and compatibility with peroxides.

The present inventors have found that when the below-described ring-fused heterocycle direct dyes are used as a hair dyes, surprisingly, the resulting hair colouring composition can impart the hair with more vivid and durable colour than general oxidative hair colouring compositions.

In addition, the present inventors have found that the below-described ring-fused heterocycle direct dyestuffs have excellent stability against alkaline peroxide, and that the hair colouring effect of the composition comprising at least one of the below-described direct dyestuffs can be further improved when one applies this composition comprising at least one peroxide and preferably having a pH value of 6.5 to 12.5, together with at least one ring-fused heterocycle direct dyestuff, because hair bleaching power derived from alkaline peroxide serves more vividness to the hair.

In one aspect of the present invention, there is thus provided a hair colouring method by using a composition comprising at least one direct dyestuff represented by the general formula (1) or a salt thereof:

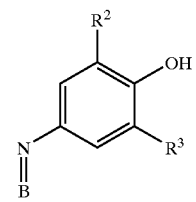

(1)

wherein B represents a heterocyclic group of the following formula (B-1), (B-2), (B-3) or (B-4):

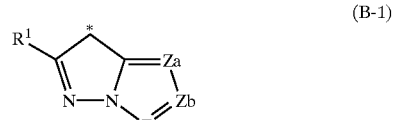

(B-1)

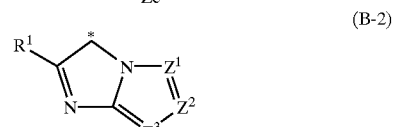

(B-2)

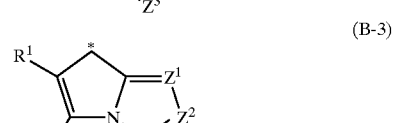

(B-3)

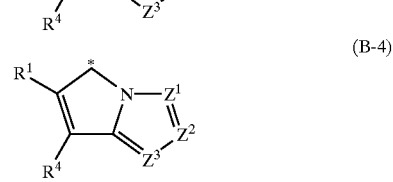

(B-4)

(wherein each of Za, Zb, Zc, $Z^1$, $Z^2$ and $Z^3$ independently represents a nitrogen atom or a group —C($R^5$)=, at least one of Zb and Zc is the group —C($R^5$)= and at least one of $Z^1$, $Z^2$ and $Z^3$ is a nitrogen atom.

$R^1$, $R^4$ and $R^5$ independently represent a hydrogen atom; a halogen atom; a $C_{1-5}$ alkyl group which may be optionally substituted by one or more of halogen atom(s), hydroxy group(s), alkoxy group(s), aryloxy group(s), amino group(s), alkylamino group(s), hydroxyalkylamino group(s), acyl group(s), acylamino group(s) or alkylsulfonylamino group(s); a $C_{1-4}$ alkoxy group; a $C_{1-4}$ alkylthio group; an arylthio group; a heteroarylthio group; a benzylthio group; an acyl group which may be optionally substituted by one or more of hydroxy group(s) or amino group(s); an acylamino group; an alkylsulfonylamino group; an acyloxy group; a carbamoyl group; an alkylaminocarbonyl group; a dialkylaminocarbonyl group; a phenyl group which may be optionally substituted by one or more of halogen atom(s), nitro group(s), sulfo group(s), alkylsulfonyl group(s), $C_{1-4}$ alkyl group(s), $C_{1-4}$ alkoxy group(s), $C_{1-3}$ fluoroalkyl group(s), amino group(s), alkylamino group(s), hydroxyalkylamino group(s) or alkylsulfonylamino group(s); an alkoxycarbonyl group which may be optionally substituted by one or more of hydroxy group(s); an aryloxycarbonyl group; a heteroaryloxycarbonyl group; a cyano group; a nitro group; a dialkylphosphinyl group; an alkylsulfinyl group; an arylsulfinyl group; a sulfamoyl group; an alkylaminosulfonyl group; a dialkylaminosulfonyl group; a carboxy group; a sulfo group; an aryloxy group which may be optionally substituted by one or more of alkoxy group(s); an heteroaryloxy group; a $C_{1-4}$ alkylamino group; an ureido group; a sulfamoylamino group; an alkoxycarbonylamino group; an aryloxycarbonylamino group; or a phosphonyl group), each of $R^2$ and $R^3$ independently represents a hydrogen atom, a $C_{1-5}$ alkyl group, an acylamino group, an alkylsulfonylamino group or an electron withdrawing group, and * represents the position which binds to the nitrogen atom in the formula (1).

In another aspect of the present invention, there is thus provided the above-described hair colouring composition.

BEST MODE FOR CARRYING OUT THE INVENTION

A group of the following formula (B-1-1) or (B-1-2) which has pyrazolotriazole structure:

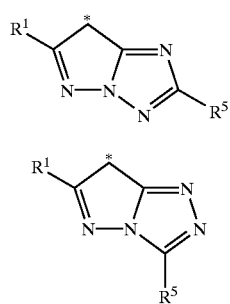

(B-1-1)

(B-1-2)

(wherein each of $R^1$, $R^5$ and * has the same meanings as described above) is preferred as the group (B-1).

A group of the following formula (B-2-1), (B-2-2) or (B-2-3) which has imidazoloazole structure:

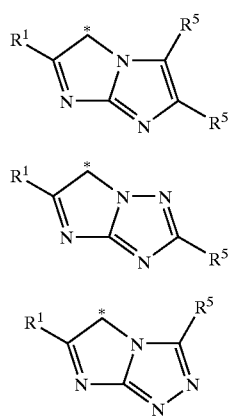

(B-2-1)

(B-2-2)

(B-2-3)

(wherein each of $R^1$, $R^5$ and * has the same meanings as described above) is preferred as the group (B-2).

A group of the following formula (B-3-1) or (B-3-2) which has pyrroloazole structure:

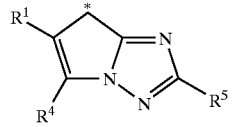

(B-3-1)

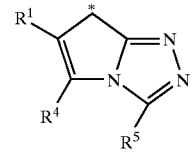

(B-3-2)

(wherein each of $R^1$, $R^4$, $R^5$ and * has the same meanings as described above) is preferred as the group (B-3).

A group of the following formula (B-4-1) or (B-4-2) which has pyrroloazole to structure:

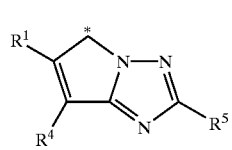

(B-4-1)

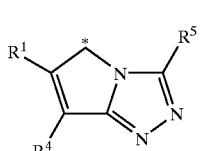

(B-4-2)

(wherein each of $R^1$, $R^4$, $R^5$ and * has the same meanings as described above) is preferred as the group (B-4).

Above all, the groups (B-1-1) and (B-1-2) which have pyrazolotriazole structure are most preferable in the light of vividness and durability of the resulting colour.

As the group represented by $R^1$, $R^4$ or $R^5$, hydrogen atom; $C_{1-5}$ alkyl group which may be optionally substituted by one or more of hydroxy group(s), alkoxy group(s), amino group(s), alkylamino group(s) or alkylsulfonylamino group(s); a $C_{1-4}$ alkoxy group; or phenyl group which may be optionally substituted by one or more of halogen atom(s), $C_{1-4}$ alkyl group(s), $C_{1-4}$ alkoxy group(s), amino group(s), alkylamino group(s) or alkylsulfonylamino group(s); are in particular preferred in the light of hair colouring intensity. Of these, $C_{1-5}$ alkyl group, which has no substituent, is most preferable in the light of hair colouring intensity.

The compound of formula (1) preferably has a pKa value of 2.5 to 9, in particular 3 to 8, most preferably 3.5 to 7 in the light of hair colouring ability and durability of the resulting colour. The hydroxy group on the benzene ring is dissociative. For this reason, an electron withdrawing group is preferable as each of $R^2$ and $R^3$. Dyes having dissociative group are called dissociative dyes.

The dissociative dye represents the dye that can release a proton and be anionic above a certain pH value. The pKa value can be determined by the following method: The sample is dissolved in a solution of a DMF/water (1/1) volume ratio to a final concentration of $2 \times 10^{-5}$ mol/l. After the resulting solution is adjusted to pH 2, using 1.0 mol/l hydrochloric acid, the solution is titrated with aqueous 1.0 mol/l sodium hydroxide solution. Recording the change of the visible ultra-violet absorption spectrum, the inflection point is determined by regression analysis.

Particularly suitable examples of the electron withdrawing group represented by $R^2$ and $R^3$ are electron withdrawing groups having Hammet's $\sigma_p$ value of not less than 0.1, such as fluorine atom, chlorine atom, bromine atom, iodine atom, alkoxycarbonyl group which may be substituted by one or more of hydroxy group(s), carbamoyl group, alkylaminocarbonyl group, dialkylaminocarbonyl group, sulfamoyl group, alkylaminosulfonyl group, dialkylaminosulfonyl group or an acyl group, wherein a fluorine atom, chlorine atom and bromine atom are most preferred in the light of hair colouring intensity. Hammet's rule is an empirical rule suggested by L. P. Hammet in 1935 in order to quantitatively discuss the effects of a substituent of a benzen derivative on the reaction or equilibrium thereof, which rule has been widely acknowledged to be true. According to the Hammet' rule, there are two kind of values, $\sigma_p$ and $\acute{o}\sigma_m$ values as a coefficient of substitution. These values are described in many books. For instance, J. A. Dean "Lange's Handbook of Chemistry", 12nd edition, 1979 (McGraw-Hill); "Kagakunoryouiki-zoukan" 122, 96–103, 1979 (Nankodo); and "Chemical Review", 91, 165–195, 1991 recite the values.

For the above reasons, particularly suitable examples of the formula (1) are represented by the following general formulae (2) or (3) or a salt thereof:

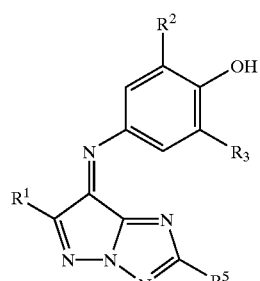

(2)

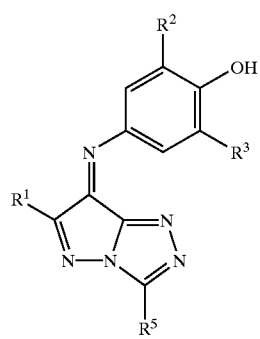

(3)

wherein each of $R^1$ and $R^5$ represents a $C_{1-5}$ alkyl group which may be optionally substituted by one or more of hydroxy group(s), alkoxy group(s), amino group(s), alkylamino group(s) or alkylsulfonylamino group(s); or phenyl group which may be optionally substituted by one or more of halogen atom(s), $C_{1-4}$ alkyl group(s), $C_{1-4}$ alkoxy group(s), amino group(s), alkylamino group(s) or alkylsulfonylamino group(s), and each of $R^2$ and $R^3$ represents an electron withdrawing group which can be selected from among fluorine atom, chlorine atom, bromine atom, iodine atom, alkoxycarbonyl group which may be substituted by one or more of hydroxy group(s), carbamoyl group, alkylaminocarbonyl group, dialkylaminocarbonyl group, sulfamoyl group, alkylaminosulfonyl group, dialkylaminosulfonyl group or an acyl group.

The definitions for $R^1$ to $R^5$ in the above-described formulas are explained as follows in more detail.

Examples of the halogen atom represented by $R^1$, $R^4$ or $R^5$ include a fluorine atom, chlorine atom, bromine atom and iodine atom. In particular, chlorine and bromine atoms are preferred.

Examples of the $C_{1-5}$ alkyl group represented by $R^1$, $R^4$ or $R^5$ include methyl group, ethyl group, propyl group, isopropyl group, butyl group, sec-butyl group, t-butyl group and pentyl group.

Examples of the substituent which may optionally substitute on the above-described $C_{1-5}$ alkyl group include chlorine atom, bromine atom, hydroxy group, methoxy group, ethoxy group, phenoxy group, amino group, methylamino group, dimethylamino group, 2-hydroxyethylamino group, bis(2-hydroxyethyl)amino group, acetyl group, acetylamino group and methanesulfonylamino group. In particular, hydroxy group, methoxy group, ethoxy group, amino group, methylamino group, dimethylamino group, 2-hydroxyethylamino group, bis(2-hydroxyethyl)amino group and methanesulfonylamino group are preferred in the light of the solubility of the dyestuff.

Examples of the $C_{1-4}$ alkoxy group represented by $R^1$, $R^4$ or $R^5$ include methoxy group, ethoxy group, propoxy group, isopropoxy group, butoxy group, sec-butoxy group and t-butoxy group. In particular, methoxy group and ethoxy groups are preferred.

Examples of the $C_{1-4}$ alkylthio group represented by $R^1$, $R^4$ or $R^5$ include methylthio group and ethylthio group.

Examples of the arylthio group represented by $R^1$, $R^4$ or $R^5$ include phenylthio group, 1-naphthylthio group and 2-naphthylthio group.

Example of the heteroarylthio group represented by $R^1$, $R^4$ or $R^5$ include 2-pyridylthio group, 3-pyridylthio group, 4-pyridylthio group, 2-imidazolothio group and 3-pyrazolothio group.

Examples of the acyl group which may be optionally substituted by one or more of hydroxy group(s) or amino group(s) represented by $R^1$, $R^4$ or $R^5$ include formyl group, acetyl group, hydroxyacetyl group, aminoacetyl group, and propionyl group.

Examples of the acylamino group represented by $R^1$, $R^2$, $R^3$, $R^4$ or $R^5$ include formylamino group, acetylamino group and propionylamino group.

Examples of the alkylsulfonylamino group represented by $R^1$, $R^2$, $R^3$, $R^4$ or $R^5$ include methanesulfonylamino group and ethanesulfonylamino group.

Examples of the acyloxy group represented by $R^1$, $R^4$ or $R^5$ include acetyloxy group and propionyloxy group.

Examples of the alkylaminocarbonyl group represented by $R^1$, $R^2$, $R^3$, $R^4$ or $R^5$ include methylaminocarbonyl group and ethylaminocarbonyl group.

Examples of the dialkylaminocarbonyl group represented by $R^1$, $R^2$, $R^{3,}$ $R^4$ or $R^5$ include dimethylaminocarbonyl group and diethylaminocarbonyl group.

Examples of the substituent which may optionally substitute on the phenyl group represented by $R^1$, $R^4$ or $R^5$ include fluorine atom, chlorine atom, bromine atom, iodine atom, nitro group, sulfo group, methanesulfonyl group, ethanesulfonyl group, methyl group, ethyl group, methoxy group, ethoxy group, trifluoromethyl group, amino group, methylamino group, dimethylamino group, 2-hydroxyethylamino group, bis(2-hydroxyethyl)amino group and methanesulfonylamino group. In particular, chlorine atom, bromine atom, amino group, methylamino group, dimethylamino group, 2-hydroxyethylamino group, bis(2-hydroxyethyl)amino group and methanesulfonyl group are preferred.

Examples of the alkoxycarbonyl group which may be substituted by one or more of hydroxy group(s) represented by $R^1$, $R^4$ or $R^5$ include methoxycarbonyl group, ethoxycarbonyl group, propoxycarbonyl group and 2-hydroxyethoxycarbonyl group.

Examples of the aryloxycarbonyl group represented by $R^1$, $R^4$ or $R^5$ include phenoxycarbonyl group, 1-naphthyloxycarbonyl group and 2-naphthyloxycarbonyl group.

Examples of the heteroaryloxycarbonyl group represented by $R^1$, $R^4$ or $R^5$ include 2-pyridyloxycarbonyl group, 3-pyridyloxycarbonyl group and 4-pyridyloxycarbonyl group.

Examples of the dialkylphosphinyl group represented by $R^1$, $R^4$ or $R^5$ include dimethylphosphinyl group and diethylphosphinyl group.

Examples of the alkylsulfinyl group represented by $R^1$, $R^4$ or $R^5$ include methylsulfinyl group and ethylsulfinyl group.

Examples of the arylsulfinyl group represented by $R^1$, $R^4$ or $R^5$ include phenylsulfinyl group.

Examples of the alkylaminosulfonyl group represented by $R^1$, $R^2$, $R^3$, $R^4$ or $R^5$ include methylaminosulfonyl group and ethylaminosulfonyl group.

Examples of the dialkylaminosulfonyl group represented by $R^1$, $R^2$, $R^3$, $R^4$ or $R^5$ include dimethylaminosulfonyl group and diethylaminosulfonyl group.

Examples of the aryloxy group which may be optionally substituted by one or more of alkoxy group(s) represented by $R^1$, $R^4$ or $R^5$ include phenoxy group, 1-naphthyloxy group, 2-naphthyloxy group and dimethoxy phenoxy group.

Examples of the heteroaryloxy group represented by $R^1$, $R^4$ or $R^5$ include 2-pyridyloxy group, 3-pyridyloxy group and 4-pyridyloxy group.

Examples of the $C_{1-4}$ alkylamino group represented by $R^1$, $R^4$ or $R^5$ include methylamino group, ethylamino group, propylamino group and butylamino group.

Examples of the alkoxycarbonylamino group represented by $R^1$, $R^4$ or $R^5$ include methoxycarbonylamino group and ethoxycarbonylamino group.

Examples of the aryloxycarbonylamino group represented by $R^1$, $R^4$ or $R^5$ include phenoxycarbonylamino group.

Examples of the ring-fused heterocycle direct dye represented by formula (1) according to the present invention include the following structures DS-1 to DS-30.

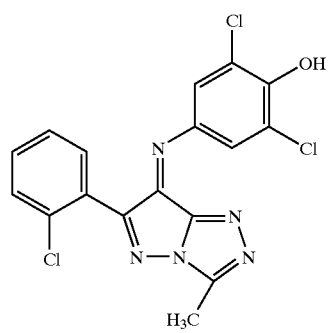

DS-1

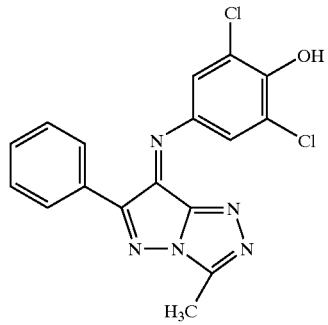

DS-2

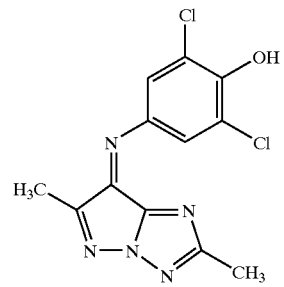

DS-3

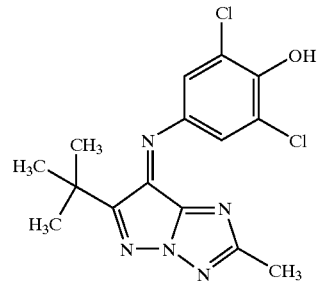

DS-4

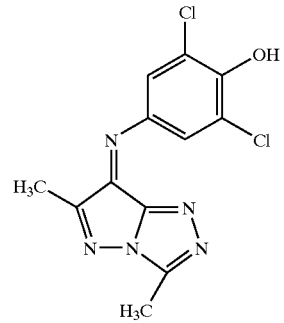

DS-5

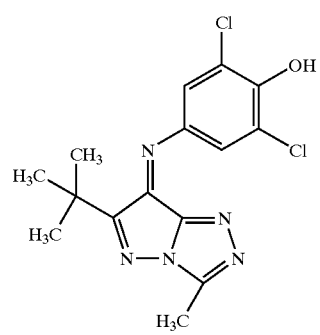

DS-6

-continued
DS-7
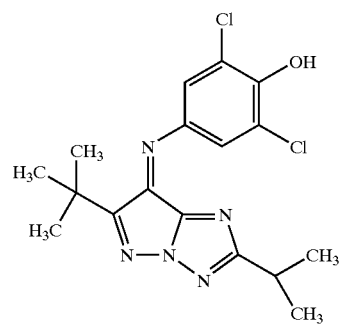
DS-8
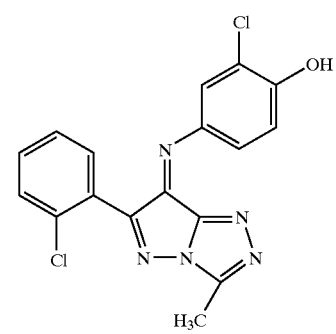
DS-9
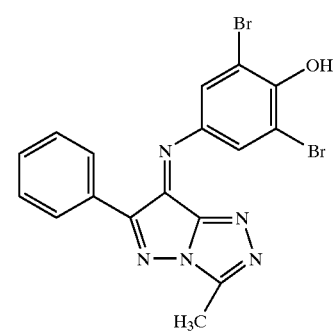
DS-10
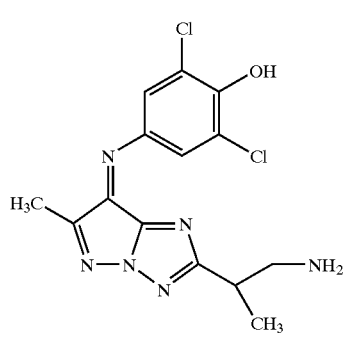
DS-11
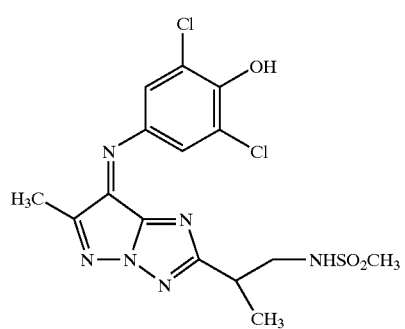
-continued
DS-12
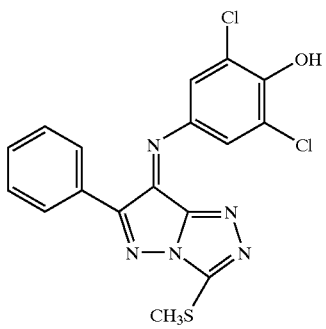
DS-13
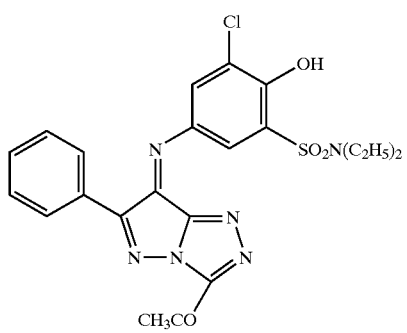
DS-14
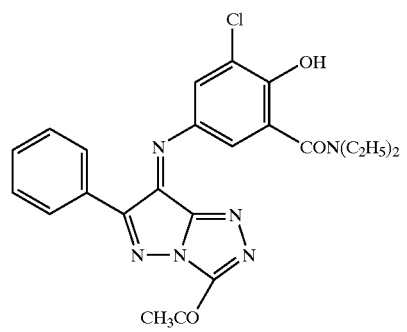
DS-15
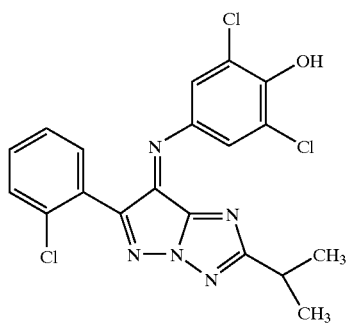
DS-16
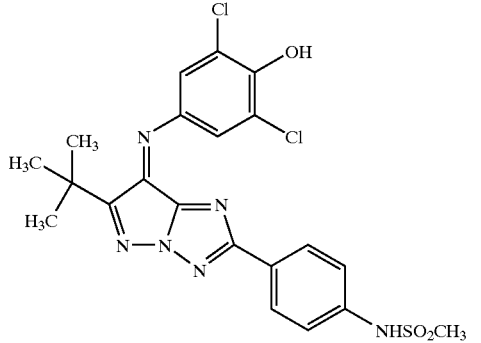

DS-17
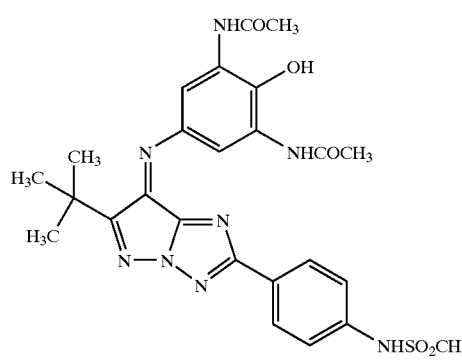
DS-18
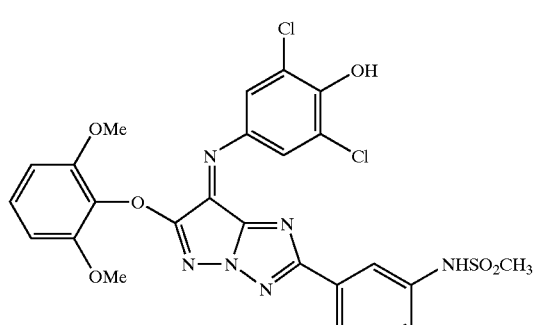
DS-19
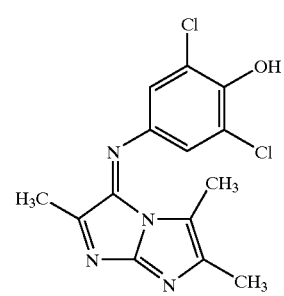
DS-20
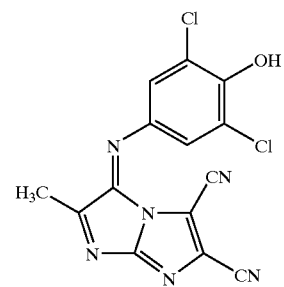
DS-21
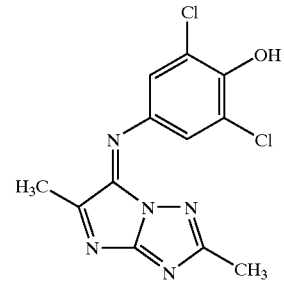
DS-22
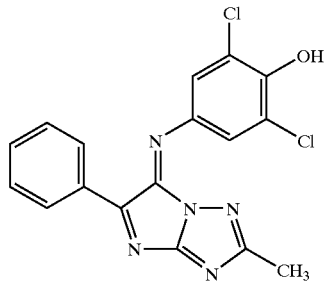
DS-23
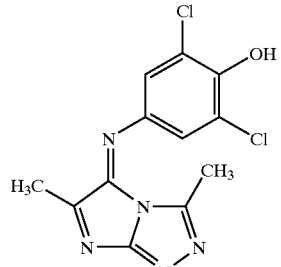
DS-24
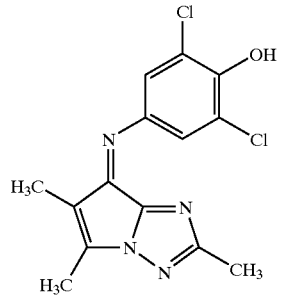
DS-25
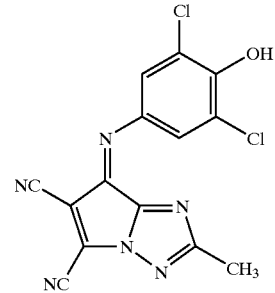
DS-26
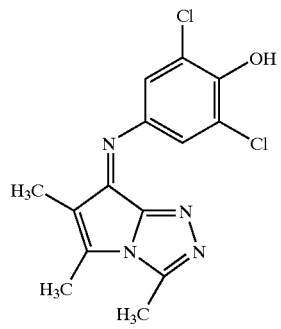

-continued
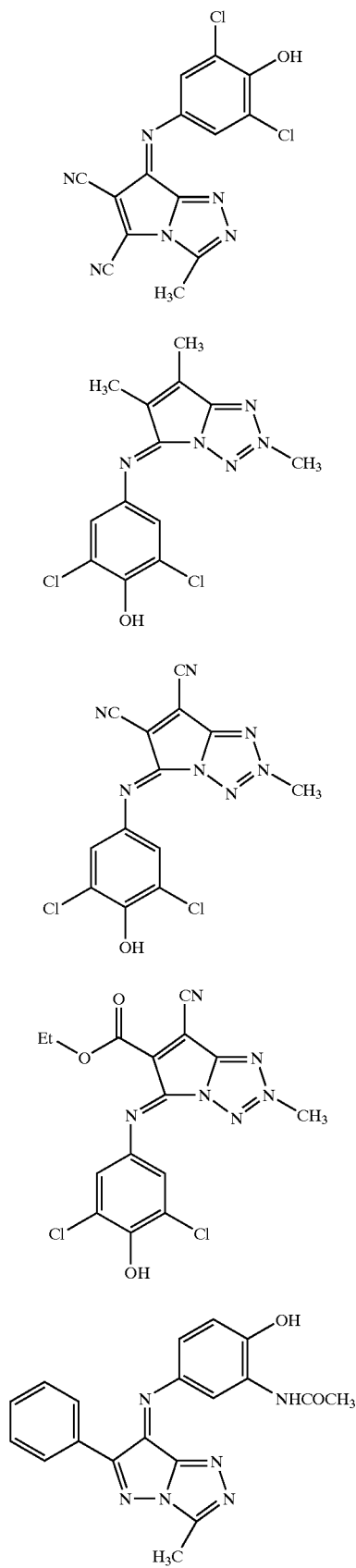
DS-27
DS-28
DS-29
DS-30
DS-31
-continued
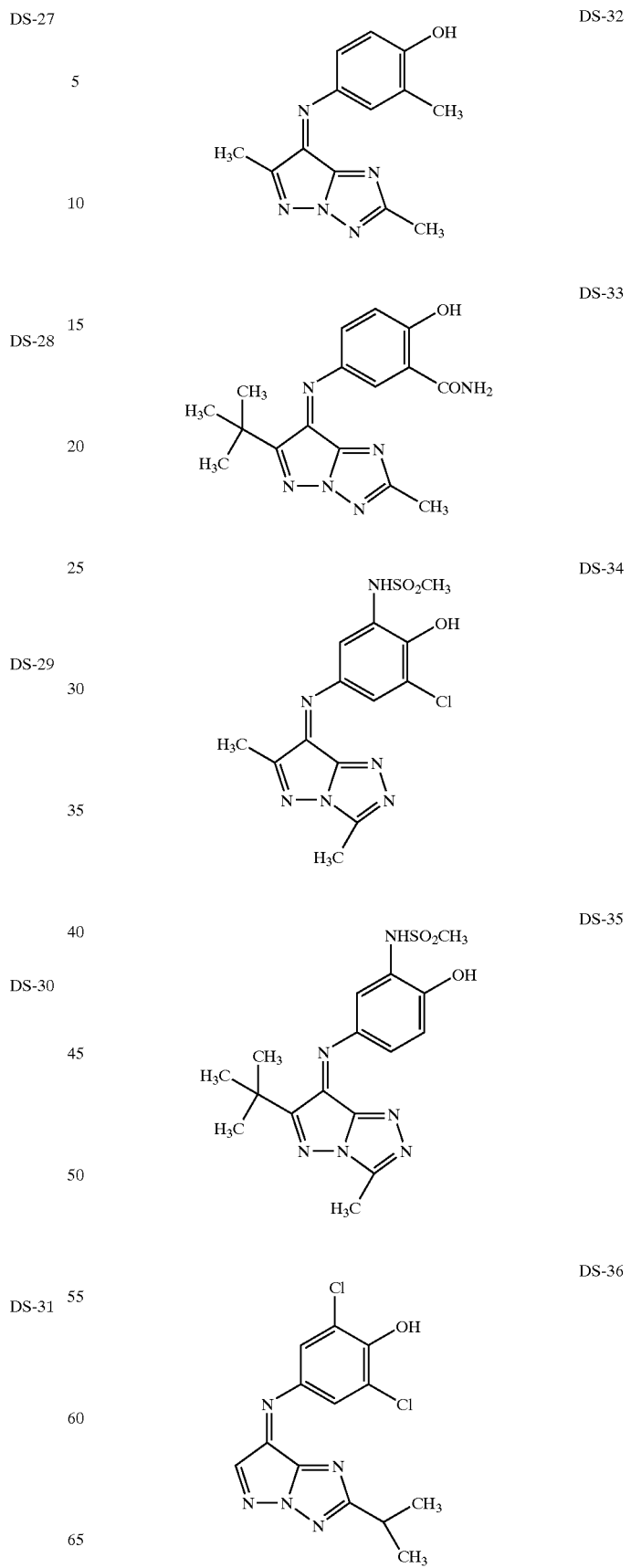
DS-32
DS-33
DS-34
DS-35
DS-36

-continued

DS-37
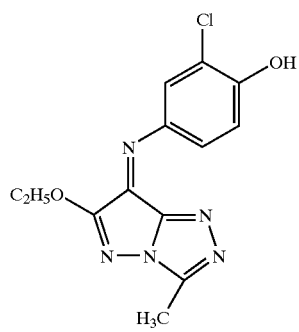

DS-38
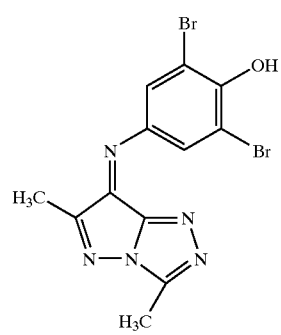

DS-39
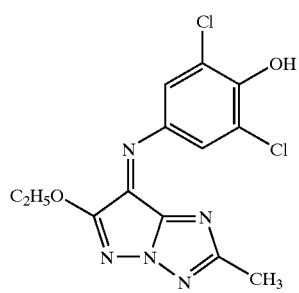

DS-40
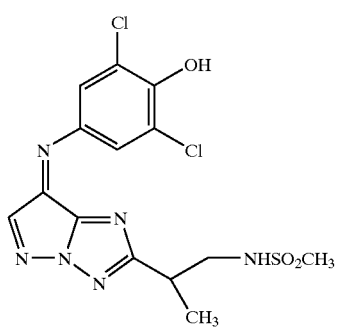

DS-41
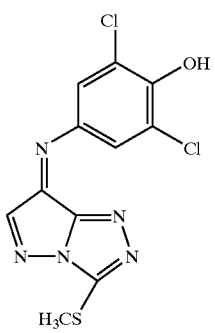

Each of the compounds of formulas (1), (2) and (3) of the present invention may be a salt of an organic or inorganic acid, or an organic or inorganic alkali. Examples of the organic or inorganic acid include hydrochloric acid, sulphuric acid, phosphoric acid, acetic acid, propionic acid, lactic acid and citric acid. Examples of the organic or inorganic alkali include ammonium hydroxide, 2-ethanolammonium hydroxide, sodium hydroxide and potassium hydroxide.

The production of the above-described ring-fused heterocycle direct dyestuffs is actually well known and is achieved via oxidative coupling of the corresponding substituted ring-fused heterocycle with the corresponding substituted aminophenol derivatives.

This oxidative coupling reaction can be achieved by, for example, the following procedure: The corresponding ring-fused heterocycle and the corresponding p-aminophenol are dissolved in an aqueous solution having pH value of approximately 7–12, then an appropriate amount of persulfate such as potassium persulfate is added to the alkaline solution. Stirring the solution for approximately 2 hours at room temperature leads to formation of the ring-fused heterocycle direct dye (1).

The ring-fused heterocycle direct dye (1) can be isolated by, for example, the following method: The resulting precipitate is collected via filtration; the precipitate is dried and then taken up in acetone. The acetone solution is filtered to remove impurities and then evaporated to leave the ring-fused heterocycle direct dye (1).

The resulting colours are thereby mainly in the range from intensive pink to intensive violet colour, but they can be varied by further addition of other dye(s).

The proportion of the above-described ring-fused heterocycle direct dyestuffs in the compositions according to the present invention is variable and depends on the dye structure and also on desired chroma; it is appropriate generally within 0.001 to 5 wt %, preferably 0.01 to 2.5 wt %, in particular 0.1 to 1 wt %. Wt % is based on the ready to use composition throughout this specification and the claims.

Beside the ring-fused heterocycle direct dye represented by the formula (1), further direct dyestuffs for hair can also additionally be used to create a wide range of colour nuances.

Concerning such direct dyestuffs, so-called "Arianor-dyestuffs" are preferred; referring to K. Schrader, "Grundlagen und Rezepturen der Kosmetika", $2^{nd}$ edition, (1989), p. 811.

Particularly suitable basic (cationic) dyestuffs are:

| | |
|---|---|
| Basic Blue 6 (C.I. No. 51,175) | Basic Blue 7 (C.I. No. 42,595) |
| Basic Blue 9 (C.I. No. 52,015) | Basic Blue 26 (C.I. No. 44,045) |
| Basic Blue 41 (C.I. No. 11,154) | Basic Blue 99 (C.I. No. 56,059) |
| Basic Brown 4 (C.I. No.21,010) | Basic Brown 16 (C.I. No. 12,250) |
| Basic Brown 17 (C.I. No. 12,251) | Basic Brown 7 (C.I. No. 75,500) |
| Basic Green 1 (C.I. No. 42,040) | Basic Red 2 (C.I. No. 50,240) |
| Basic Red 12 (C.I. No. 48,070) | Basic Red 22 (C.I. No. 11,055) |
| Basic Red 76 (C.I. No. 12,245) | Basic Violet 1 (C.I. No. 42,535) |
| Basic Violet 3 (C.I. No. 42,555) | Basic Violet 10 (C.I. No. 45,170) |
| Basic Violet 14 (C.I. No. 42,510) | Basic Yellow 57 (C.I. No. 12,719) | as well as dyestuffs disclosed in patent EP 0618 464 B1.

Of course, the use of direct dyestuffs from plants and/or anionic (acidic) direct dyestuffs for hair is also possible. The following dyestuffs can be used as suitable anionic dyestuffs:

| | |
|---|---|
| Acid Black 1 (C.I. No. 20,470) | Acid Blue 1 (C.I. No. 42,045) |
| Food Blue 5 (C.I. No. 42,051) | Acid Blue 9 (C.I. No. 42,090) |
| Acid Blue 74 (C.I. No. 73,015) | Acid Red 18 (C.I. No. 16,255) |
| Acid Red 27 (C.I. No. 16,185) | Acid Red 87 (C.I. No. 45,380) |
| Acid Red 92 (C.I. No.45,410) | Acid Orange 7 (C.I. No. 15,510) |
| Acid Violet 43 (C.I. No. 60,730) | Acid Yellow 1 (C.I. No.10,316) |
| Acid Yellow 23 (C.I. No. 19,140) | Acid Yellow 3 (C.I. No. 47,005) |
| Food Yellow 8 (C.I. No. 14,270) | Acid Orange 24 (C.I. No. 20,170) |
| Acid Green 25 (C.I. No. 61,570) | Acid Orange 7 (C.I. No. 15,510) |
| Solvent Red 73 (C.I. No. 45,425:1) | Acid Red 95 (C.I. No. 45,425) |
| Solvent Red 43 (C.I. No. 45,380:2) | Solvent Red 48 (C.I. No. 45,410:1) |
| Acid Red 33 (C.I. No. 17,200) | |
| Acid Yellow 73 (C.I. No. 45,350:1 and C.I. No. 45,350) | |
| Food Red 1 (C.I. No. 14,700) | Food Yellow 3 (C.I. No. 15,985) |

Also using vegetable dyestuffs, which include, for example, henna (red or black), alkanna root, laccaic acid (Stocklack), Indigo, logwood root powder, madder root and rhubarb powder, etc., alone or in combination with synthetic direct dyestuffs, is possible.

These direct dyestuffs can be usually likewise used in an amount of 0.005 to 5 wt %, preferably 0.05 to 2.5 wt %, in particular 0.1 to 1 wt % based on the whole composition, which is presented in the form of solution, dispersion, emulsion, gel or aerosol, for application.

The compositions according to the present invention can also comprise at least one oxidative dyestuff intermediate, i.e. a developer and/or a coupler substance.

Examples of the developer include, in particular, 1,4-diaminobenzene, 2,5-diaminotoluene, tetraaminopyrimidine, triaminohydroxypyrimidine, 1,2,4-triaminobenzene, 2-(2,5-diaminophenyl)ethanol, 2-(2-hydroxyethylamino)-5-aminotoluene, 1-amino-4-bis-(2-hydroxyethyl)aminobenzene or water-soluble salts thereof.

Examples of the coupler include resorcin, 2-methylresorcin, 4-chlororesorcin, 2-amino-4-chlorophenol, 4-(N-methylamino)phenol, 2-aminophenol, 3-aminophenol, 1-methyl-2-hydroxy-4-aminobenzene, 3-(N,N-dimethylamino)phenol, 4-amino-3-methylphenol, 5-amino-2-methylphenol, 6-amino-3-methylphenol, 3-amino-2-methylamino-6-methoxypyridine, 2-amino-3-hydroxypyridine, 4-aminodiphenylamine, 4,4'-diaminodiphenylamine, 2-dimethylamino-5-aminopyridine, 2,6-diaminopyridine, 1,3-diaminobenzene, 1-amino-3-(2-hydroxyethylamino)benzene, 1-amino-3-[bis(2-hydroxyethyl)amino]benzene, alpha-naphthol, 1,4-diamino-2-chlorobenzene, 4,6-dichlororesorcin, 1,3-diaminotoluene, 1-hydroxynaphthalene, 4-hydroxy-1,2-methylenedioxybenzene, 1,5-dihydroxynaphthalene, 1,7-dihydroxynaphthalene, 2,7-dihydroxynaphthalene, 2,4-diamino-3-chlorophenol and/or 1-methoxy-2-amino-4-(2-hydroxyethylamino)benzene. The above-described examples do not limit the present invention to these compounds.

Developers and couplers are preferably comprised in the molar ratio of 1:3 to 5:1, in particular 1:1 to 3:1, and their proportion incorporated in the hair colouring composition of the present invention can amount to 0.05 to 5 wt %, and it depends upon desired colour.

The above-described ring-fused heterocycle direct dyestuff (1) has an excellent stability against alkaline peroxide, so they are compatible with peroxide, which can provide hair bleaching ability at the same time as hair colouring. For this purpose, the hair colouring composition of the present invention can comprise at least one peroxide with at least one of the above-described ring-fused heterocycle direct dyestuff (1).

As peroxides for the above-described hair colouring composition, all of diluted solutions, emulsions or gels of hydrogen peroxide can be used, but also further peroxides such as alkaline-earth peroxides, for example magnesium peroxide, urea peroxides or melaminperoxide, etc. can be used in appropriate stoichiometric quantities. Additionally, to increase the level of hair bleaching, in particular persulfates such as ammonium persulfate, potassium persulfate and sodium persulfate can be incorporated. The combined use of hydrogen peroxide and the above-described persulfates is preferable in the light of providing an exceptional bleaching power. It is particularly preferable that pH value of the composition is adjusted between 6.5 to 12.5, preferably 8 to 11.

As the hair-components which comprise persulfate, the components, which are mixed as powders with the aqueous hydrogen peroxide, e.g. 6 wt % of aqueous $H_2O_2$ solution, are particularly suitable referring, for example, the monography of K. Schrader, "Grundlagen und Rezepturen der Kosmetika", $2^{nd}$ edition (1989), pp. 815–823.

The hair colouring composition of the present invention can also contain surface-active substances. An anionic, nonionic, cationic, amphoteric or zwitter-ionic surfactant can be incorporated in the hair colouring composition of the present invention, and the above-described surfactants are compatible if used together.

Examples of anionic surfactant include sulfate-, sulfonate-, carboxylate- and alkyl phosphate-type, which are usually used in shampoos.

For example, the well-known $C_{10-18}$ alkyl sulfates and in particular the appropriate ether sulfates, for example $C_{12-14}$ alkylether sulfate, laurylether sulfate, in particular with 1 to 4 ethyleneoxide groups in the molecule can be listed as the sulfate-type anionic surfactant. Furthermore, monoglyceride (ether)sulfate, fatty acid amide sulfates which are produced by ethoxylation and following sulfate introduction to the corresponding fatty acid alkanolamide, and their alkali salts as well as salts of long-chained mono and dialkyl phosphates, which represent mild detergent and which can be applied on the skin, also can be used.

Examples of the suitable anionic surfactant include alpha-olefinsulfonate or its salts and, in particular, alkali salts of sulfosuccinic acid half-ester, for example disodium salt of the monooctylsulfo succinate and alkali salts of long-chained monoalkylethoxysulfo succinate.

Examples of the suitable carboxylate type surfactants include alkylpolyethercarboxylic acid or their salts represented by the following formula (4) and alkamidopolyether-carboxylic acid or their salts represented by the following formula (5):

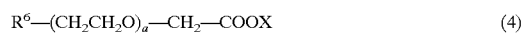

$$R^6-(CH_2CH_2O)_a-CH_2-COOX \qquad (4)$$

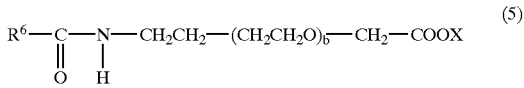

(wherein $R^6$ represents a $C_{8-20}$ alkyl group, preferably a $C_{12-14}$ alkyl group, X represents a hydrogen atom or a cation of sodium, potassium, magnesium or ammonium, which can be optionally hydroxyalkyl-substituted, a represents a number of 1 to 20, preferably 2 to 17, and b represents a number of 1 to 10, preferably 2.5 to 5.)

Such products are well known and have been on the market for a long time, for example "AKYPO®" and "AKYPO-SOFT®" under the trade name.

Also $C_{8-20}$ acyl isethionate and likewise sulfofatty acid and their ester can be used, however, in the mixture with other surfactants.

Also mixtures of several anionic surfactants, for example mixtures of an alpha-olefin sulfate and a sulfa succinate, preferably in the relation of 1:3 to 3:1, or an ether sulfate and a polyetheroarboxylic acid or an alkylamidoethercarboxylic acid can be used.

Furthermore, the anionic surfactants, which are generally used as liquid body cleaning agents, can be used, and the outline of these surfactants is disclosed in the monography of K. Schrader, "Grundlagen und Rezepturen der Kosmetika", $2^{nd}$ edition (1989, Huethig Buchverlag), pp. 683 to 691.

Concerning the concentration of anionic surfactant, the preferable amount thereof is between 5 and 50 wt %, in particular between 10 and 25 wt %. The anionic surfactant is preferably incorporated in tinting shampoos of the present invention, and the preferable amount thereof is between 5 and 30 wt %, in particular between 7.5 to 25 wt %, particularly preferentially between 10 to 20 wt %, calculated on the whole composition.

Examples of suitable nonionic surfactant include alkylpolyglucosides with the following general formula (6):

(wherein $R^7$ represents a $C_{8-20}$, preferably a $C_{10-14}$ alkyl group, Z represents a $C_{5-6}$ saccharide, p represents a number from 0 to 10, and q represents a number from 1 to 5, preferably 1.1 to 2.5. Further suitable nonionic surfactant for the composition of the present invention is $C_{10-22}$ fatty-alkyl ethoxylate.)

and $C_{10-22}$ fatty-alcohol ethers are, under the trade names, the "Laureth", "Myristeth", "Oleth", "Ceteth", "Deceth", "Steareth" and "Ceteareth" after the CTFA nomenclature, which are added the number of ethyleneoxides, e.g. Laureth-16, and the average number of the ethyleneoxides is appropriate thereby between 2.5 to 25, preferably 10 to 20.

Other additionally along-usable nonionic surfactant are e.g. sorbitan ester such as polyethyleneglycol-sorbitan stearate, fatty acid polyglycol ester or also ester of fatty acid and mixed-polymerized polyglycol from ethylene oxide and propylene oxide, as they are on the market, for example, under the trade name "Pluronics®".

Further additionally applicable surfactant is amine oxide. Such amine oxides belong to the state of the art for a long time, for example to $C_{12-18}$ alkyldimethylamine oxide such as Lauryldimethylamine oxide, $C_{12-18}$ alkylamidopropylamine oxide or alkylamidoethylamine oxides, $C_{12-18}$ alkyldi(hydroxyethyl)amine oxide or alkyldi(hydroxypropyl)amine oxide or also amine oxides which have groups of ethylene oxides and/or propylene oxides in their alkyl chain. Suitable amine oxides are on the market, for example under the trade name of "Ammonyx®", "Aromox®" or "Genaminox®".

Further optional surfactant-constituents are fatty acid-mono and dialkanolamide, like cocofattyacid-monoethanolamide and myristic acid-monoisopropanolamide.

Examples of suitable amphoteric or zwitter-ionic surfactant include, in particular, well known betaines such as fatty acid-amidoalkylbetaine and sulfobetaine, for example Laurylhydroxysulfobetaine; also, long-chained alkylamino acids such as cocoaminoacetate, cocoaminopropionate, sodium cocoamphopropionate and sodium cocoamphoacetate are listed as suitable examples.

In particular betaines or sulfobetaines represented by the following formulas (7) to (10):

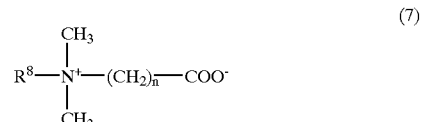

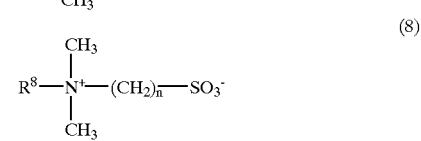

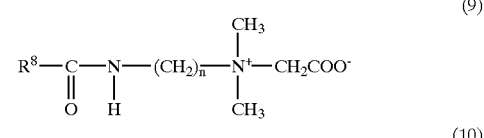

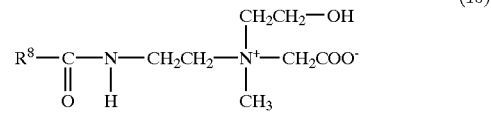

(wherein $R^8$ represents a $C_{8-18}$ alkyl group and n represents 1 to 3)

Examples of preferable fatty acid-amidoalkylbetaine include, in particular, cocoamidopropylbetaine, cocoamphoacetate and cocoamphopropionate, and sodium salts thereof. Preferable mixing ratio of cocoamidopropylbetaine and cocoamphoacetate is 3:1 to 1:3, and in particular, 2:1 to 1:1 in the weight ratio.

Examples of suitable cationic surfactant include long-chained quaternized ammonium compounds, which can be used alone or in the combination, like cetyltrimethylammonium chloride, dimethylstearylammonium chloride, trimethylcetylammonium bromide, stearyltrimethylammonium chloride, dimethylstearylbenzylammonium chloride, benzytetradecyldimethylammonium chloride, dimethyl di-hydrogenated-tallow ammonium chloride, lauryldimethylbenzylammonium chloride, behenyltrimethylammonium chloride, lauryltrimethylammonium chloride, tris-(oligooxy-ethyl)alkylammonium phosphate, cetylpyridinium chloride, etc.

Quaternized ammonium salts disclosed in EP-A 472,107 are also well suited. Other examples of suitable long-chained ammonium compound include esters or amides of quaternized ammonium compounds represented by the general formula (11) or (12);

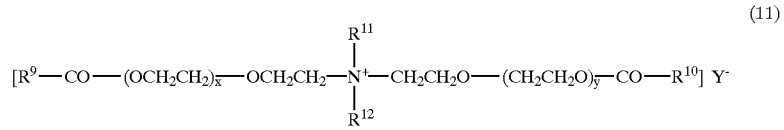

-continued

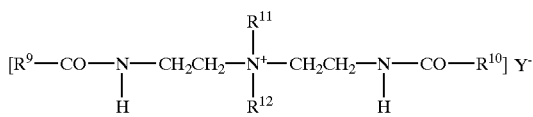

(12)

(wherein $R^9$ and $R^{10}$ independently represent a $C_{8-22}$ alkyl group or alkenyl group which may be optionally substituted by hydroxy group, $R^{11}$ and $R^{12}$ independently represent a $C_{1-3}$ alkyl group or a group $-CH_2-CH_2-O-(CH_2CH_2O)_z-H$, each of x, y and z independently represents 0 to 5 and $Y^-$ represents an anion).

The anion $Y^-$ is preferably a halide ion such as $Cl^-$ or $Br^-$, lower alkyl sulfate ion e.g. methyl sulfate ion and ethyl sulfate ion, or an alkyl phosphate ion, however, also general different anions can be assigned.

It is particularly preferred that in the formula (11) $R^9$ and $R^{10}$ each represent an oleyl group or a $C_{12-18}$ alkyl group, $R^{11}$ represents a methyl group and $R^{12}$ represents a group $-CH_2-CH_2-O-(CH_2CH_2O)_z-H$. These compounds are well known and put on the market under the trade name of, for example, "Schercoquat®", "Dehyquart F30®" and "Tetranyl®". The application of these "Esterquats" for hair preservative agents is actually well known and, for example, disclosed in WO-A 93/10748, WO-A 92/06799 and WO-A 94/16677.

In case that the composition of the present invention does not relate to the tinting shampoo, nonionic, amphoteric or zwitter-ionic and cationic surfactants are preferably used in a quantity of between 0.5 to 5 wt % calculated on the whole composition.

A further desirable constituent for the hair colouring compositions of the present invention is a $C_{3-6}$ alkanediol or its ether, in particular, a mono-$C_{1-3}$ alkylether.

Preferential solvents for the composition of the present invention are 1,2- and 1,3-propanediol, 1-methoxy-2-propanol, 1-ethoxy-2-propanol, 1,3- and 1,4-butanediol, diethyleneglycol and its monomethyl and monoethyl ether as well as dipropyleneglycol and its monomethyl and monomethyl ether. The proportion of these diols are appropriate preferably between 0.5 and 30, more preferably 1 to 15 wt %, in particular 5 to 10 wt % on the whole composition. In addition to these $C_{3-6}$ alkanediols or their ethers, also monoalcohols such as ethanol, 1-propanol and 2-propanol; polyalcohols such as glycerine and hexanetriol; ethylcarbitol; benzyl alcohol; benzyloxyethanol; propylene carbonate (4-methyl-1,3-dioxan-2-on); n-alkylpyrrolidone; and urea are also suitable and can be used.

Further possible components are cationic, anionic, non-ionic and amphoteric polymers, and they can be incorporated preferably in an amount of from 0.1 to 5 wt %, in particular, 0.25 to 2.5 wt % of the whole colouring composition. The composition of the present invention can comprise also further preservative agents such as oils and fats. Such are, for example, sun flower oil, almond oil, peach kernel oil, wheat germ oil, macadamia nut oil, night Evening Primrose oil, jojoba oil, castor oil, or also olive or soybean oil, lanolin and its derivatives, likewise mineral oils such as paraffin oil and Vaseline®.

The composition of the present invention can comprise synthetic oils and waxes, for example, silicone oils, polyethylene glycols, etc.

Further suitable hydrophobic compounds, in particular, fatty acid esters such as Isopropyl myristate, -palmitate, -stearate and -isostearate, oleyl oleate, isocetyl stearate, hexyl laurate, dibutyl adipate, dioctyl adipate, myristyl myristate, oleyl erucate, polyethylene glycol and polyglyceryl fatty acid esters such as PEG-7-glycerylcocoate, cetyl palmitate, etc. can be also used.

If the composition of the present invention is present in the form of an emulsion, the compositions of the present invention may comprise generally used emulsifying agents. The composition according to the present invention can comprise also long-chained fatty acids. As fatty acids, $C_{10-24}$, particularly $C_{12-22}$ fatty acids are preferable, and they can be incorporated in an amount of 0.5 to 15 wt % in particular 1 to 10 wt %, calculated on the whole composition. Behenic acid and stearic acid are particularly suitable, however, other fatty acids for example myristic acid, palmitic acid, oleic acid or also mixtures of natural or synthetic fatty acids such as coco-fatty acid also can be incorporated.

The composition according to the present invention preferably has a viscosity of 1,000 to 60,000 mPa s, in particular 5,000 to 50,000 mPa s, above all 10,000 to 40,000 mPa s at 20° C., measured by using the Brookfield rotary viscometer with a spindle of No.5 at 5 rpm.

The pH value is adjusted preferably to a neutral or basic range of between 6.5 and 12.5 for example between 7.8 and 12, in particular between 8 and 11. Examples of preferable alkalization agent include ammonia, monoethanolamine and alkali carbonates and -hydrogencarbonates such as sodium carbonate, potassium carbonate, sodium hydrogencarbonate and potassium hydrogencarbonate. However, also different alkalization agents such as di- and triethanolamine as well as further hydroxyalkanolamines can be used.

When the composition of the present invention relates to tinting shampoo, it can generally comprise, beside the above-enumerated surface-active substances, anionic surfactant.

A preferable execution form of the tinting shampoo according to the present invention contains preferably a mixture of at least one anionic surfactant above-mentioned and a $C_{8-22}$ acylaminocarboxylic acid or their water-soluble salts, preferably in a quantity from 0.5 to 10, in particular 1 to 7.5 wt %, calculated on the whole composition.

Particularly preferable N-acylaminocarboxylic acid or their water-soluble salt is the N-lauroylglutamate, in particular the sodium salt thereof.

Further suitable N-acylaminocarboxylic acids are, for example, N-lauroylsarcosinate, N—$C_{12-18}$-acyl aspartic acid, N-myristoylsarcosinate, N-oleoylsarcosinate, N-lauroylmethylalanine, N-lauroyllysine and N-lauroylaminopropylglycine, preferably in the form of their water-soluble alkali metal salt or ammonium salt, in particular sodium salts.

The composition of the present invention can further comprise well-known additives for cosmetics, such as thickeners, perfumes, stabilizers, solubilizing-aid agents, natural and/or synthetic polymers, chelating agents, etc. The composition of these substances is basically well known and for example described in the monography by K. Schrader, pp. 796–798.

The hair colouring composition of the present invention can be applied in all well-known hair colouring media, in particular solutions, creams, emulsions, pastes, gels, (foam-) aerosols, etc.

The hair colouring composition of the present invention can be prepared in a conventional manner into a one-part composition, a two-part composition having a first-part component containing an alkalization agent and a second-part component containing a oxidizing agent, or a three-part composition having, in addition to these two components, a powdery oxidizing agent such as persulfate. The direct ring-fused heterocycle dye (1) can be incorporated in either one or both of these components of the two-part or three-part composition.

The one-part type is applied to the hair directly, while the two- or three-part type is applied to the hair after mixing these parts upon hair colouring.

The induction period of this hair colouring composition is preferably 10 to 60 minutes; it can be reduced by thermal effect. Afterwards the hair is washed or rinsed and dried.

EXAMPLES

The following examples serve to illustrate the present invention.

The dyes obtained according to the synthetic examples I to III and the examples using the dyes of DS-1 to DS-41 are according to the present invention. On the other hand, the dyes NDS-1 and NDS-2 obtained in accordance with the synthetic examples IV and V and the examples using these dyes are not according to the present invention, these serve for comparison purposes only.

Synthetic Example I

3-Methyl-6-phenyl-1H-pyrazolo[5,1-c][1,2,4]triazole (0.5 g) was dissolved in alkaline water at pH 12 (50 mls). To this was added 4-amino-2,6-dichlorophenol (0.5 g) with stirring. To this mixture was added potassium persulfate (0.2 g), upon which, the solution turned dark purple. The mixture was left stirring for 2 hrs, before collecting the resulting precipitate via filtration. The dark brown precipitate was dried and then taken up in acetone. The acetone solution was filtered to remove impurities and then evaporated to leave pyrazolotriazole direct dye DS-2 as a dark brown crystalline powder.

solution was filtered to remove impurities and then evaporated to leave pyrazolotriazole direct dye DS-1 as a dark brown crystalline powder.

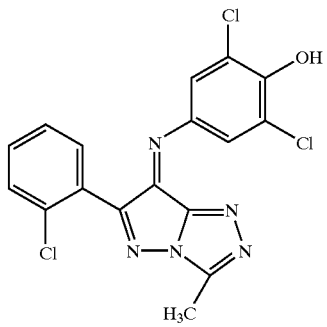

DS-1

Synthetic Example III

7-Chloro-2,6-dimethyl-1H-pyrazolo[1,5-b][1,2,4]triazole (24.4 g) and potassium carbonate (98.8 g) were added in mixed solution of water (100 ml), ethyl acetate (120 ml), and ethanol (60 ml). To this was added 4-amino-2,6-dichlorophenol (27.9 g) with stirring. To this mixture was added aqueous solution of ammonium persulfate (39.3 g/water 100 ml) slowly over 40 min, upon which, the solution turned dark purple. After the mixture was left stirring for 2 hrs, water (500 ml) was added. To this was added concentrated hydrochloric acid (75 ml) slowly, upon which, the solution turned brownish yellow. The mixture was left stirring for 30 mins, before collecting the resulting precipitate via filtration. The wet brownish yellow precipitate was taken up in acetonitrile. After the acetonitrile solution was refluxed for 20 mins, the acetonitrile solution was cooled to room temperature. The resulting precipitate was collected via filtration and dryed. Pyrazolotriazole direct dye DS-3 as a yellow powder (39.6 g, 89% yield).

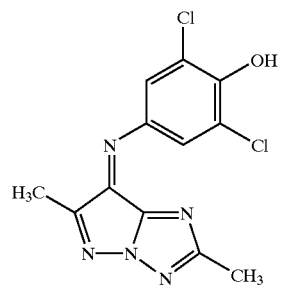

DS-3

The dyes DS-4 to DS-41 were produced with a similar method as Synthetic examples I, II and III.

Synthetic Example IV (Not According to the Invention)

6-(2-chlorophenyl)-3-Methyl-1H-pyrazolo[5,1-c][1,2,4]triazole (0.5 g) was dissolved in alkaline water at pH 12 (50 mls). To this was added 2,5-diaminotoluene (0.5 g) with stirring. To this mixture was added potassium persulfate (0.2 g), upon which, the solution turned dark purple. The mixture was left stirring for 2 hrs, before collecting the resulting precipitate via filtration. The dark brown precipitate was dried and then taken up in acetone. The acetone solution was filtered to remove impurities and then evaporated to leave

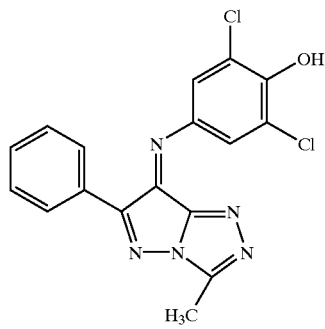

DS-2

Synthetic Example II 6-(2-chlorophenyl)-3-Methyl-1H-pyrazolo[5,1-c][1,2,4]triazole (0.5 g) was dissolved in alkaline water at pH 12 (50 mls). To this was added 4-amino-2,6-dichlorophenol (0.5 g) with stirring. To this mixture was added potassium persulfate (0.2 g), upon which the solution turned dark purple. The mixture was left stirring for 2 hrs, before collecting the resulting precipitate via filtration. The dark brown precipitate was dried and then taken up in acetone. The acetone pyrazolotriazole direct dye NDS-1 as a dark brown crystalline powder.

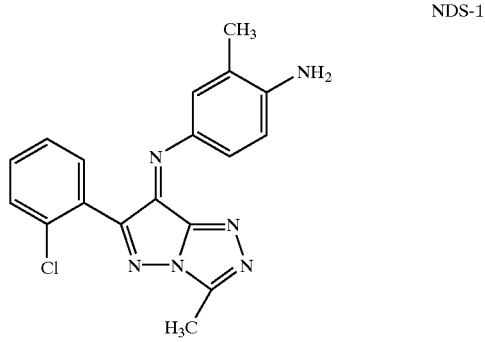

NDS-1

Synthetic Example V (Not According to the Invention)

6-(2-chlorophenyl)-3-Methyl-1H-pyrazolo[5,1-c][1,2,4] triazole (0.5 g) was dissolved in alkaline water at pH 12 (50 mls). To this was added N,N-diethyl-p-phenylenediamine (0.5 g) with stirring. To this mixture was added potassium persulfate (0.2 g), upon which, the solution turned dark purple. The mixture was left stirring for 2 hrs, before collecting the resulting precipitate via filtration. The dark brown precipitate was dried and then taken up in acetone. The acetone solution was filtered to remove impurities and then evaporated to leave pyrazolotriazole direct dye NDS-2 as a dark brown crystalline powder.

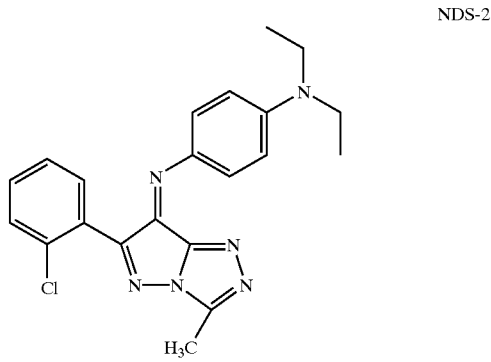

NDS-2

Examples 1–4

Dyeing

TABLE 1

|  | 1 | 2 | 3* | 4* |
|---|---|---|---|---|
| Dyestuff DS-2 | 0.01 g | / | / | / |
| Dyestuff DS-1 | / | 0.01 g | / | / |
| Dyestuff NDS-1* | / | / | 0.01 g | / |
| Dyestuff NDS-2* | / | / | / | 001 g |
| Benzyl Alcohol | 0.5 g | 0.5 g | 0.5 g | 0.5 g |
| Water | up to 10 g | up to 10 g | up to 10 g | up to 10 g |
| Ammonia | to pH 10 | to pH 10 | to pH 10 | to pH 10 |

*Not according to the invention

For examples 1 to 4, an undamaged white goat hair tress was submerged in the solution for 20 mins at 30° C. After this time the tress was shampoo rinsed and then dried. L, a and b values of resulting coloured tresses were measured by Minolta colour-measuring instrument and the value of delta E, which is a measure of the chroma as well known, was calculated in usual way for each example (this will apply equally to every example hereinafter). Table 2 shows the results.

TABLE 2

|  | L | a | b | Delta E | Colouring result |
|---|---|---|---|---|---|
| Before | 80 | 1 | 14 | — | While goat hair |
| Example 1 | 47 | 46 | −21 | 66 | Bright vivid magenta |
| Example 2 | 46 | 49 | −22 | 69 | Bright vivid magenta |
| Example 3 | 70 | 13 | 5 | 18 | Dull light pink |
| Example 4 | 65 | 12 | −2 | 24 | Dull light pink |

Each composition of examples 1 and 2 imparted a bright vivid magenta colour, while the compositions of comparative examples 3 and 4 imparted only a dull colour with very weak pink tones.

Comparing these examples shows the surprising superiority of the direct dyes that have dissociative protons according to the present invention (examples 1 and 2) in contrast to the structurally similar direct dyes, which have no dissociative protons (examples 3 and 4).

Examples 5 to 6

Dyeing

A base of the following composition was prepared.

TABLE 3

|  | 5 | 6 |
|---|---|---|
| Dyestuff DS-3 | 0.04 g | / |
| Dyestuff DS-4 | / | 0.04 g |
| Ethanol | 0.1 g | 0.1 g |
| Ammonia (35%) | 0.5 g | 0.5 g |
| Benzyl alcohol | 0.5 g | 0.5 g |
| Water | up to 10 g | up to 10 g |

Each composition was applied to undamaged white goat tresses and undamaged human blond hair for 15 mins at 50° C. After this time the tress was shampooed, rinsed and then dried. Table 4 and 5 show the results.

TABLE 4

| (undamaged white goat tress) | | | | |
|---|---|---|---|---|
|  | Colouring results | | | |
| Initial white goat tress | L = 81 | a = 1 | b = 14 | |
| Example 5 | L = 44 | a = 53 | b = 17 | delta E = 72 |
| Example 6 | L = 43 | a = 52 | b = 9 | delta E = 69 |

TABLE 5

| (undamaged human blond hair) | | | | |
|---|---|---|---|---|
|  | Colouring results | | | |
| Initial human blond hair | L = 43 | a = 6 | b = 17 | |
| Example 5 | L = 35 | a = 21 | b = 6 | delta E = 21 |
| Example 6 | L = 33 | a = 25 | b = 6 | delta E = 23 |

Each composition of Examples 5 and 6, imparted a bright vivid magenta colour to both the undamaged white goat hair and the undamaged human blond hair.

Examples 7 to 15

Dyeing Goat and Human Hair the following general composition was prepared for each of pyrazolotriazole direct dyes DS-3, DS-4, DS-6, DS-7 and DS-12 to DS-16.

TABLE 6

General Composition

| | |
|---|---|
| Dyestutf | 0.02 g |
| Benzyl alcohol | 0.5 g |
| Ethanol | 0.5 g |
| Ammonia(25%) | 0.3 g |
| Water | up to 10 g |

Each composition was applied to one undamaged white goat tress for 20 mins at 50° C. (1 g of tress was covered by 1.5 to 2 g of composition). After 20 mins the tresses were rinsed, shampoo washed and then dried before the colour was assessed. Table 7 shows the result.

TABLE 7

| Example | Dyestuff | L | a | b | Delta E | Colouring Result |
|---|---|---|---|---|---|---|
| 7 | DS-3 | 30 | 54 | -12 | 81 | Bright, intense magenta |
| 8 | DS-4 | 38 | 60 | 16 | 75 | Bright, intense magenta |
| 9 | DS-6 | 57 | 42 | -7 | 55 | Bright pink |
| 10 | DS-7 | 50 | 50 | -8 | 60 | Pink |
| 11 | DS-12 | 48 | 29 | -26 | 59 | Violet |
| 12 | DS-13 | 50 | 29 | -23 | 55 | Violet |
| 13 | DS-14 | 59 | 16 | -22 | 54 | Pale violet |
| 14 | DS-15 | 51 | 33 | -17 | 55 | Violet |
| 15 | DS-16 | 55 | 41 | -3 | 52 | Bright pink |

Examples 16 and 17

Dyeing with Hydrogen Peroxide

TABLE 8

| | 16 | 17 |
|---|---|---|
| Dyestuff DS-2 | 0.012 g | / |
| Dyestuff DS-1 | / | 0.012 g |
| Ethanol | 0.5 g | 0.5 g |
| Benzyf Alcohol | 0.5 g | 0.5 g |
| Hydrogen Peroxide (50%) | 0.6 g | 0.6 g |
| Water | up to 10 g | up to 10 g |
| Ammonia (25%) | to pH 10 | to pH 10 |

An undamaged white goat hair tress was submerged in the solution for 20 mins at 30° C. After this time the tress was shampoo rinsed and then dried. Table 9 shows the results.

TABLE 9

| | L | a | b | Delta E | Colouring result |
|---|---|---|---|---|---|
| Before | 80 | 1 | 14 | / | White goat hair |
| Example 16 | 40 | 48 | -26 | 73.5 | Bright vivid magenta |
| Example 17 | 48 | 50 | -27 | 71.5 | Bright vivid magenta |

Each composition of examples 16 and 17 imparted a bright vivid magenta colour.

Examples 18 to 21

Compatibility with Hydrogen Peroxide

The following general compositions in Table 10 were prepared for each of pyrazolotriazole direct dyes DS-4 and DS-6.

TABLE 10

| | 18 | 19 | 20 | 21 |
|---|---|---|---|---|
| Dyestuff DS-4 | 0.02 g | / | 0.02 g | / |
| Dyestuff DS-6 | / | 0.02 g | / | 0.02 g |
| Benzyl alcohol | 0.5 g | 0.5 g | 0.5 g | 0.5 g |
| Ethanol | 0.5 g | 0.5 g | 0.5 g | 0.5 g |
| Ammonia(25%) | 0.3 g | 0.3 g | 0.3 g | |
| Hydrogen Peroxide (50%) | / | / | 0.6 g | 0.6 g |
| Water | up to 10 g | up to 10 g | up to 10 g | up to 10 g |

Each composition was applied to one undamaged human blond hair for 20 mins at 50° C. After 20 mins the tresses were rinsed, shampoo washed and then dried before the colour was assessed. Table 11 shows the change in red colour (a value).

TABLE 11

(undamaged human blond hair)

| | Colouring results | | |
|---|---|---|---|
| | Dyestuff | $H_2O_2$ | Delta a |
| Example 18 | DS-4 | None | 27 |
| Example 19 | DS-6 | None | 15 |
| Example 20 | DS-4 | 3 wt % | 39 |
| Example 21 | DS-6 | 3 wt % | 30 |

The dye DS-4 and DS-6 were stable to alkaline peroxide, so the compositions of Example 20 and 21 with peroxide imparted more vivid red colour than the compositions of Example 18 and 19 which comprised no peroxide.

Examples 22–25

Compatibility with Persulfate

The following compositions were prepared.

TABLE 12

| | Example | | | |
|---|---|---|---|---|
| | 22 | 23 | 24 | 25* |
| Dyestuff DS-2 | 0.04 g | / | / | / |
| Dyestuff DS-3 | / | 0.04 g | / | / |
| Dyestuff DS-4 | / | / | 0.04 g | / |
| Goldwell Oxyplatin Bleach powder[1) | 2.5 g | 2.5 g | 2.5 g | 2.5 g |
| Goldwell Topchic 6% Peroxide Base | 3.5 g | 3.5 g | 3.5 g | 3.5 g |
| Benzyl Alcohol | 0.3 g | 0.3 g | 0.3 g | 0.3 g |

*Not according to the invention
[1)powder containing ammonium persulfate 18%, potassium persulfate 40%, magnesium peroxide 1%

Compositions 22–25 were applied to black Chinese hair tresses and left for 30 mins at 50° C. After this time the tresses were shampoo rinsed and then dried. Table 13 shows the results.

TABLE 13

| | Colouring result | | |
|---|---|---|---|
| | L | a | b |
| Before | 19 | 1.5 | 1.9 |
| Example 22 | 33 | 21 | 10 |

TABLE 13-continued

| | Colouring result | | |
|---|---|---|---|
| | L | a | b |
| Example 23 | 30 | 23 | 9 |
| Example 24 | 29 | 22 | 10 |
| Example 25* | 45 | 10 | 24 |

*Not according to the invention

Compositions of examples 22 to 24 imparted a vivid magenta colour. These compositions delivered significant bleaching with intense red colouration.

Examples 26 and 27

Compatibility with Oxidative Dyes

A base of the following composition was prepared.

TABLE 14

| | 26 | 27* |
|---|---|---|
| Dyestuff DS-4 | 0.02 wt % | / |
| p-phenylenediamine | 0.05 wt % | 0.05 wt % |
| Resorcinol | 0.05 wt % | 0.05 wt % |
| o-aminophenol | 0.4 wt % | 0.4 wt % |
| p-aminophenol | 0.4 wt % | 0.4 wt % |
| Benzyl alcohol | 5.0 wt % | 5.0 wt % |
| Ethanol | 5.0 wt % | 5.0 wt % |
| Hydrogen Peroxide (50%) | 6.0 wt % | 6.0 wt % |
| Ammonium Hydroxide (30%) | to pH 10 | to pH 10 |
| Water | balance | balance |

*Not according to the invention

Both compositions were applied to white goat tresses for 15 mins at 50° C. After this time the tresses were shampoo rinsed and then dried. Table 15 shows the results.

TABLE 15

| | Colouring result | | |
|---|---|---|---|
| Example 26 | L = 32 | a = 15 | b = 6 |
| Example 27* | L = 31 | a = 7 | b = 13 |

*Not according to the invention

Composition of example 26 imparted a red auburn colour, while composition of comparative example 27 imparted a light brown with no red tones.

The hair colouring compositions according to the present invention also provide the long lasting brilliant colours based on characteristics of ring-fused heterocycle direct dyes against hair washing and environmental influences such as exposure to the sun, sweat, rain, etc. when compared with conventional direct dyestuffs.

Examples 28 and 29

The wash fastness of DS-4 on damaged hair was compared with a standard oxidative combination. Thus, the following formulations were applied to permed human blonde hair for 15 mins at 50° C.

TABLE 16

| | 28 | 29* |
|---|---|---|
| Dyestuff DS-4 | 0.02 g | / |
| N-Hydroxyethyl-3,4-diaminopyrazole | / | 0.01 g |
| 1-Naphthol | / | 0.01 g |
| Benzyl Alcohol | 0.5 g | 0.5 g |
| Sodium Lauryl Sulphate | 0.01 g | 0.01 g |
| Ammonia (25%) | 0.5 g | 0.5 g |
| Hydrogen Peroxide (50%) | 0.6 g | 0.6 g |
| Water | up to 10 g | up to 10 g |

*Not according to the invention

Both tresses were dyed an intense magenta colour. The tresses were then put through a shampoo washing protocol and the colour loss from washing measured. The shampoo washing protocol consists of applying 0.1 g shampoo per gram of hair and massaging into the hair for 30 secs followed by 30 secs of rinsing under 40° C. water. This process is repeated 20 times. The L, a and b values before and after and the colour change after the treatment cycle calculated, Table 17 shows the results.

TABLE 17

| | L | a | b | Delta E fade |
|---|---|---|---|---|
| Original Hair; before dyeing | 48 | 6 | 18 | |
| Example 28; after dyeing | 27 | 31 | −2 | |
| Example 28; after washing | 27 | 32 | −3 | 1.7 |
| Example 29*; after dyeing | 31 | 29 | 2 | |
| Example 29*; after washing | 41 | 22 | 8 | 14 |

*Not according to the invention

Surprisingly, the dyes of the invention are extremely resistant to fading from washing when compared to standard oxidative technology.

Example 30

Measurement of pKa Value pKa values of the dyestuffs DS-3 to DS-6, DS-7 and DS10 were determined by the following method: The dye was dissolved in a solution of a DMF/water (1/1) volume ratio to a final concentration of $2 \times 10^{-5}$ mol/l. After the resulting solution was adjusted to pH 2, using 1.0 mol/l hydrochloric acid, the solution was titrated with aqueous 1.0 mol/l sodium hydroxide solution. Recording the change of the visible ultra-violet absorption spectrum, the inflection point was determined by regression analysis. Table 18 shows the results.

TABLE 18

| Dyestuff | pKa value determined |
|---|---|
| DS-3 | 3.78 |
| DS-4 | 3.88 |
| DS-5 | 4.34 |
| DS-7 | 3.92 |
| DS-10 | 3.38 |

What is claimed is:
1. A hair colouring method comprising applying to the hair a composition comprising, as a direct dyestuff, an ring-fused heterocycle direct dyestuff represented by the following general formula (1) or a salt thereof:

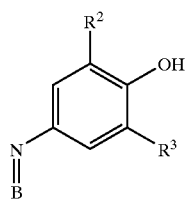

(1)

wherein B represents a heterocyclic group of the following formula (B-1), (B-2), (B-3) or (B-4):

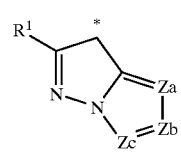

(B-1)

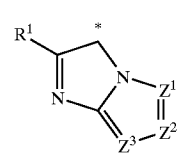

(B-2)

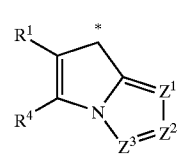

(B-3)

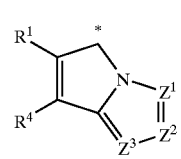

(B-4)

wherein each of Za, Zb, Zc, $Z^1$, $Z^2$ and $Z^3$ independently represents a nitrogen atom or a group —C($R^5$)═, at least one of Zb and Zc is the group —C($R^5$)═ and at least one of $Z^1$, $Z^2$ and $Z^3$ is a nitrogen atom, $R^1$, $R^4$ and $R^5$ independently represent a hydrogen atom; a halogen atom; a $C_{1-5}$ alkyl group which may be optionally substituted by one or more of halogen atom(s), hydroxy group(s), alkoxy group(s), aryloxy group(s), amino group(s), alkylamino group(s), hydroxyalkylamino group(s), acyl group(s), acylamino group(s) or alkylsulfonylamino group(s); a $C_{1-4}$ alkoxy group; a $C_{1-4}$ alkylthio group; an arylthio group; a heteroarylthio group; a benzylthio group; an acyl group which may be optionally substituted by one or more of hydroxy group(s) or amino group(s); an acylamino group; an alkylsulfonylamino group; an acyloxy group; a carbamoyl group; an alkylaminocarbonyl group; a dialkylaminocarbonyl group; a phenyl group which may be optionally substituted by one or more of halogen atom(s), nitro group(s), sulfo group(s), alkylsulfonyl group(s), $C_{1-4}$ alkyl group(s), $C_{1-4}$ alkoxy group(s), $C_{1-3}$ fluoroalkyl group(s), amino group(s), alkylamino group(s), hydroxyalkylamino group(s) or alkylsulfonylamino group(s); an alkoxycarbonyl group which may be optionally substituted by one or more of hydroxy group(s); an aryloxycarbonyl group; a het- eroaryloxycarbonyl group; a cyano group; a nitro group; a dialkylphosphinyl group; an alkylsulfinyl group; an arylsulfinyl group; a sulfamoyl group; an alkylaminosulfonyl group; a dialkylaminosulfonyl group; a carboxy group; a sulfo group; an aryloxy group which may be optionally substituted by one or more of alkoxy group(s); an heteroaryloxy group; a $C_{1-4}$ alkylamino group; an ureido group; a sulfamoylamino group; an alkoxycarbonylamino group; an aryloxycarbonylamino group; or a phosphonyl group, each of $R^2$ and $R^3$ independently represents a hydrogen atom, a $C_{1-5}$ alkyl group, an acylamino group, an alkylsulfonylamino group or an electron withdrawing group, and * represents the position which binds to the nitrogen atom in the formula (1).

2. A hair colouring method according to claim 1, wherein B represents a group of the following formula (B-1-1) or (B-1-2) which has pyrazolotriazole structure:

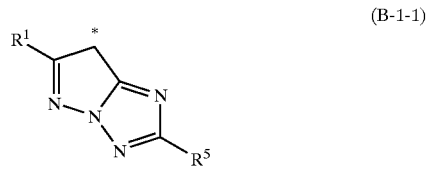

(B-1-1)

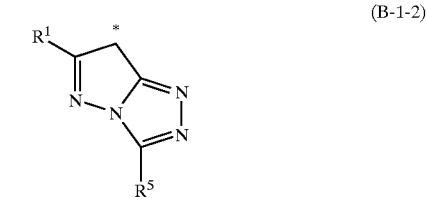

(B-1-2)

a group of the following formula (B-2-1), (B-2-2) or (B-2-3) which has imidazoloazole structure:

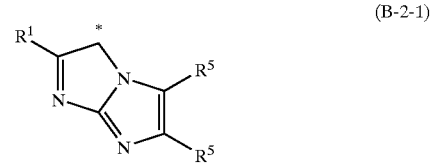

(B-2-1)

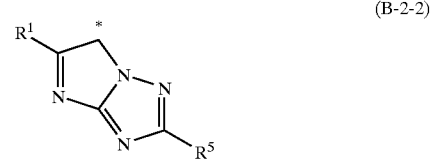

(B-2-2)

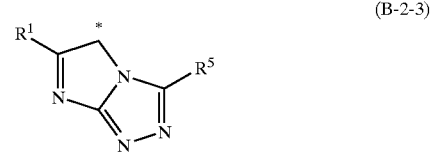

(B-2-3)

a group of the following formula (B-3-1) or (B-3-2) which has pyrroloazole structure;

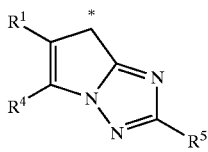
(B-3-1)

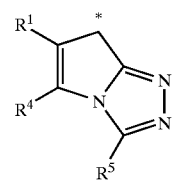
(B-3-2)

or a group of the following formula (B-4-1) or (B-4-2) which has pyrroloazole structure:

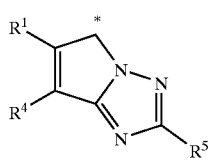
(B-4-1)

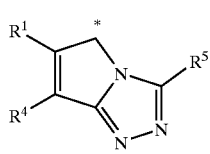
(B-4-2)

wherein each of $R^1$, $R^4$, $R^5$ and * has the same meanings as described in claim 1.

3. A hair colouring method according to claim 1, wherein the ring-fused heterocycle direct dyestuff is represented by the following general formula (2) or (3):

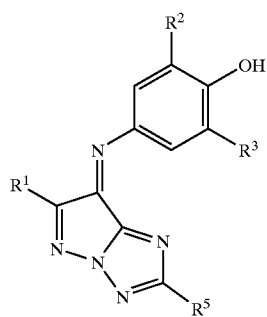
(2)

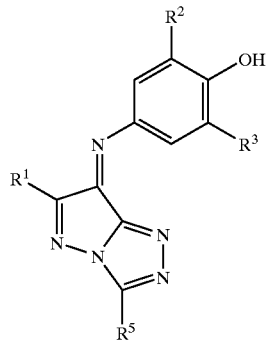
(3)

wherein each of $R^1$ and $R^2$ represents a $C_{1-5}$ alkyl group which may be optionally substituted by one or more of hydroxy group(s), alkoxy group(s), amino group(s), alkylamino group(s), or alkylsulfonylamino group(s); or a phenyl group which may be optionally substituted by one or more of halogen atom(s), $C_{1-4}$ alkyl group(s), $C_{1-4}$ alkoxy group(s), amino group(s), alkylamino group(s) or alkylsulfonylamino group(s), and each of $R^2$ and $R^3$ represents an electron withdrawing group which can be selected from among fluorine atom, chlorine atom, bromine atom, iodine atom, alkoxycarbonyl group which may be substituted by one or more of hydroxy group(s), carbamoyl group, alkylaminocarbonyl group, dialkylaminocarbonyl group, sulfamoyl group, alkylaminosulfonyl group, dialkylaminosulfonyl group or an acyl group.

4. A hair colouring method according to any one of the claims 1 to 3, wherein the hair colouring composition comprises 0.001 to 5 wt % of at least one ring-fused heterocycle direct dyestuff based on the whole composition.

5. A hair colouring composition comprising 0.001 to 5 wt % of at least one ring-fused heterocycle direct dyestuff based on the whole composition, wherein at least one ring-fused heterocycle direct dyestuff is represented by the following general formula (1) or a salt thereof:

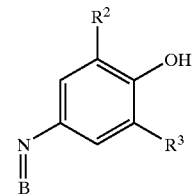
(1)

wherein B represents a heterocyclic group of the following formula (B-1), (B-2), (B-3) or (B-4):

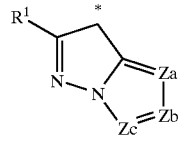
(B-1)

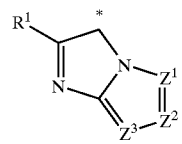
(B-2)

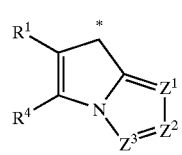
(B-3)

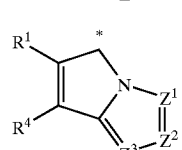
(B-4)

wherein each of Za, Zb, Zc, $Z^1$, $Z^2$ and $Z^3$ independently represents a nitrogen atom or a group —$C(R^5)$=, at least one of Zb and Zc is the group —$C(R^5)$= and at least one of $Z^1$, $Z^2$ and $Z^3$ is a nitrogen atom, R¹, R⁴ and R⁵ independently represent a hydrogen atom; a halogen atom; a C$_{1-5}$ alkyl group which may be optionally substituted by one or more of halogen atom(s), hydroxy group(s), alkoxy group(s), aryloxy group(s), amino group(s), alkylamino group(s), hydroxyalkylamino group(s), acyl group(s), acylamino group(s) or alkylsulfonylamino group(s); a C$_{1-4}$ alkoxy group; a C$_{1-4}$ alkylthio group; an arylthio group; a heteroarylthio group; a benzylthio group; an aryl group which may be optionally substituted by one or more of hydroxy group(s) or amino group(s); an acylamino group; an alkylsulfonylamino group; an acyloxy group; a carbamoyl group; an alkylaminocarbonyl group; a dialkylaminocarbonyl group; a phenyl group which may be optionally substituted by one or more of halogen atom(s), nitro group(s), sulfo group(s), alkylsulfonyl group(s), C$_{1-4}$ alkyl group(s), C$_{1-4}$ alkoxy group(s), C$_{1-3}$ fluoroalkyl group(s), amino group(s), alkylamino group(s), hydroxyalkylamino group(s) or alkylsulfonylamino group(s); an alkoxycarbonyl group which may be optionally substituted by one or more of hydroxy group(s); an aryloxycarbonyl group; a heteroaryloxycarbonyl group; a cyano group; a nitro group; a dialkylphosphinyl group; an alkylsulfinyl group; an arylsulfinyl group; a sulfamoyl group; an alkylaminosulfonyl group; a dialkylaminosulfonyl group; a carboxy group; a sulfo group; an aryloxy group which may be optionally substituted by one or more of alkoxy group(s); an heteroaryloxy group; a C$_{1-4}$ alkylamino group; an ureido group; a sulfamoylamino group; an alkoxycarbonylamino group; an aryloxycarbonylamino group; or a phosphonyl group, each of R² and R³ independently represents a hydrogen atom, a C$_{1-5}$ alkyl group, an acylamino group, an alkylsulfonylamino group or an electron withdrawing group, and * represents the position which binds to the nitrogen atom in the formula (1).

6. A hair colouring method according to any one of claims 1–3, wherein the hair colouring composition further comprises at least one peroxide.

7. A hair colouring composition according to claim 5, wherein the hair colouring composition further comprises at least one oxidative dye intermediate.

8. A hair colouring method according to claim 4, wherein the hair colouring composition further comprises at least one peroxide.

9. A hair colouring composition according to claim 5, wherein

B represents a group of the following formula (B-1-1) or (B-1-2) which has pyrazolotriazole structure:

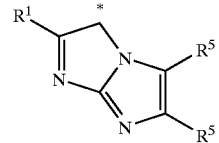
(B-1-1)

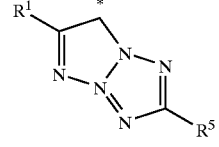
(B-1-2)

a group of the following formula (B-2-1), (B-2-2) or (B-2-3) which has imidazoloazole structure:

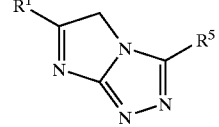
(B-2-1)

(B-2-2)

(B-2-3)

a group of the following formula (B-3-1) or (B-3-2) which has pyrroloazole structure;

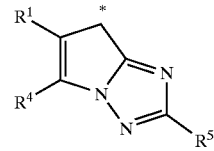
(B-3-1)

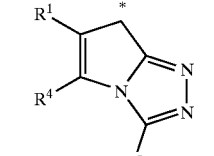
(B-3-2)

or a group of the following formula (B-4-1) or (B-4-2) which has pyrroloazole structure:

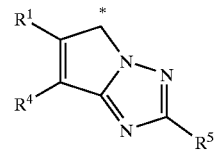
(B-4-1)

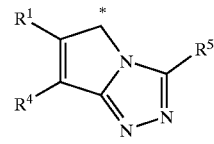
(B-4-2)

wherein each of R¹, R⁴, R⁵ and * has the same meanings as described in claim 5.

10. A hair colouring composition according to claim 5, wherein the ring-fused heterocycle direct dyestuff is represented by the following general formula (2) or (3):

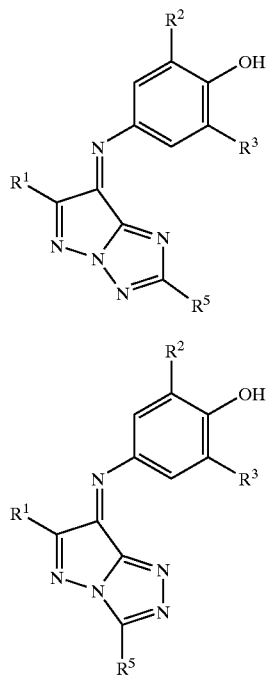

wherein each of $R^1$ and $R^5$ represents a $C_{1-5}$ alkyl group which may be optionally substituted by one or more of hydroxy group(s), alkoxy group(s), amino group(s), alkylamino group(s) or alkylsulfonylamino group(s); or a phenyl group which may be optionally substituted by one or more of halogen atom(s), $C_{1-4}$ alkyl group(s), $C_{1-4}$ alkoxy group(s), amino group(s), alkylamino group(s) or alkylsulfonylamino group(s), and each of $R^2$ and $R^3$ represents an electron withdrawing group which can be selected from among fluorine atom, chlorine atom, bromine atom, iodine atom, alkoxycarbonyl group which may be substituted by one or more of hydroxy group(s), carbamoyl group, alkylaminocarbonyl group, dialkylaminocarbonyl group, sulfamoyl group, alkylaminosulfonyl group, dialkylaminosulfonyl group or an aryl group.

11. A hair colouring composition according to claim 5, which further comprises at least one peroxide.

12. A hair colouring composition according to claim 5, which further comprises at least one direct dye other than the direct dyestuff of general formula (I), selected from the group consisting of basic dyestuffs, anionic dyestuffs, and vegetable dyestuffs.

13. A hair colouring composition according to claim 5, which further comprises at least one surfactant selected from the group consisting of anionic, nonionic, cationic, amphoteric, and zwitterionic surfactants.

14. A hair colouring composition according to claim 5, which further comprises a cationic, anionic, nonionic or amphoteric polymer.

15. A hair colouring composition according to claim 5, which is a one-part, two-part, or three-part composition.

* * * * *